(12) United States Patent
Jun

(10) Patent No.: US 10,864,067 B2
(45) Date of Patent: Dec. 15, 2020

(54) BODILY FLUID COLLECTION SYSTEM

(71) Applicant: Sunny Jun, Los Altos, CA (US)

(72) Inventor: Sunny Jun, Los Altos, CA (US)

(73) Assignee: Sunny Jun, Los Altos, CA (US)

( * ) Notice: Subject to any disclaimer, the term of this patent is extended or adjusted under 35 U.S.C. 154(b) by 316 days.

(21) Appl. No.: 15/812,571

(22) Filed: Nov. 14, 2017

(65) Prior Publication Data

US 2018/0140409 A1  May 24, 2018

Related U.S. Application Data

(60) Provisional application No. 62/424,803, filed on Nov. 21, 2016.

(51) Int. Cl.
| | |
|---|---|
| *A61D 19/00* | (2006.01) |
| *A61D 19/02* | (2006.01) |
| *A61B 10/00* | (2006.01) |
| *A61F 5/453* | (2006.01) |
| *C12N 5/076* | (2010.01) |
| *A61B 17/43* | (2006.01) |

(52) U.S. Cl.
CPC ........ *A61D 19/021* (2013.01); *A61B 10/0058* (2013.01); *A61D 19/027* (2013.01); *A61B 17/43* (2013.01); *A61F 5/453* (2013.01); *C12N 5/061* (2013.01)

(58) Field of Classification Search
CPC .. A61D 19/021; A61D 12/022; A61D 19/027; A61F 5/453; A61B 10/007; A61B 10/0058; A61B 17/43; A41D 13/1138; A61J 7/0046; A61J 7/0053
See application file for complete search history.

(56) References Cited

U.S. PATENT DOCUMENTS

| | | | |
|---|---|---|---|
| 3,343,539 A | * | 9/1967 | Moorhouse .......... A61D 19/027 604/211 |
| 4,341,211 A | | 7/1982 | Kline |
| 5,397,312 A | * | 3/1995 | Rademaker .......... A61M 31/00 604/218 |
| 7,172,573 B1 | | 2/2007 | Lamb |
| 7,666,160 B2 | | 2/2010 | Rajala et al. |
| 8,801,627 B2 | | 8/2014 | Wiegerinck et al. |

(Continued)

FOREIGN PATENT DOCUMENTS

WO      WO-0117443 A1  *  3/2001  ............. A61B 17/43

*Primary Examiner* — Benjamin J Klein
(74) *Attorney, Agent, or Firm* — Levine Bagade Han LLP

(57) ABSTRACT

Bodily fluid collection systems are described where the system may be used for collecting and transferring sperm into a syringe. The syringe is configured to have a distal collection tip which is gently tapered or radiused to present a smooth and atraumatic surface and which is specifically configured and shaped to be inserted within and received by the collection receptacle. The distal collection tip has a shape which corresponds directly to a tapered reservoir defined at the bottom of the collection receptacle such that a distal opening defined through the tip is optimally positioned within the concentrated bodily fluid pooled within the reservoir for collection. Moreover, the gentle taper of the collection tip may present an atraumatic surface for inhibiting damage to the sperm contained within the ejaculate as the sperm is suctioned into the distal opening for insemination into the female.

20 Claims, 12 Drawing Sheets

(56) References Cited

U.S. PATENT DOCUMENTS

| | | | |
|---|---|---|---|
| 8,939,940 B2 | 1/2015 | Haury et al. | |
| 8,979,734 B2 | 3/2015 | Minow | |
| 9,125,688 B2 | 9/2015 | Fowler | |
| 9,415,885 B2 | 8/2016 | Py | |
| 2004/0040985 A1* | 3/2004 | Gatton, Jr. | A61J 7/0046 |
| | | | 222/209 |
| 2006/0039833 A1 | 2/2006 | Yong | |
| 2006/0287610 A1* | 12/2006 | Wiegerinck | A61B 10/02 |
| | | | 600/563 |
| 2007/0031895 A1* | 2/2007 | Herr et al. | A61B 10/0058 |
| | | | 435/7.2 |
| 2011/0224648 A1 | 9/2011 | Secci | |
| 2012/0078136 A1* | 3/2012 | Sánchez Serrano | |
| | | | A61B 10/0058 |
| | | | 600/580 |
| 2015/0265386 A1* | 9/2015 | Schmitt | A61D 19/021 |
| | | | 604/349 |
| 2015/0320443 A1 | 11/2015 | Brown et al. | |
| 2015/0320444 A1* | 11/2015 | Brown | A61B 17/43 |
| | | | 600/35 |
| 2016/0081880 A1* | 3/2016 | Dominy | A61J 7/0007 |
| | | | 241/30 |

\* cited by examiner

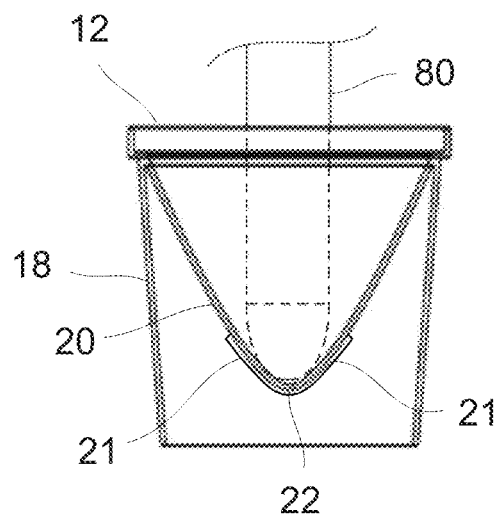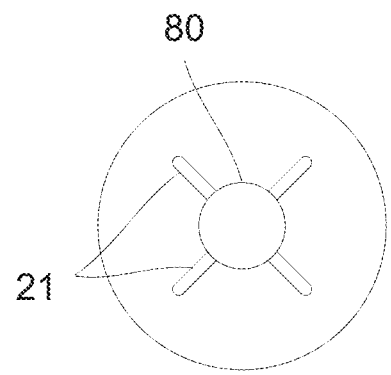
FIG. 5A  FIG. 5B
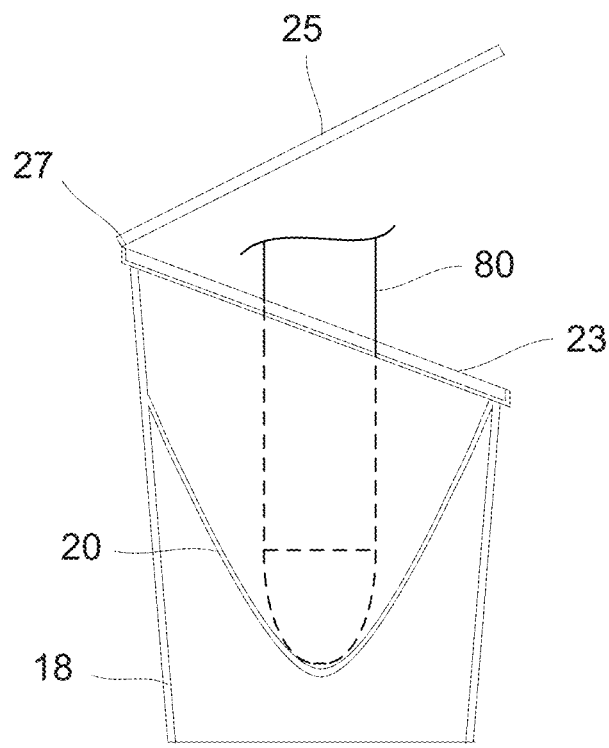
FIG. 5C

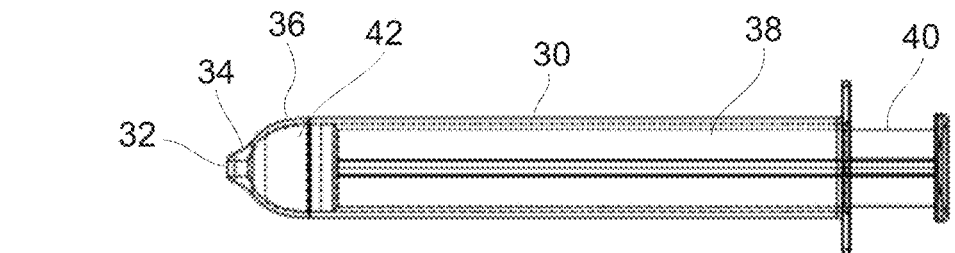
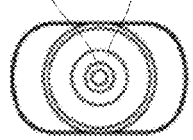 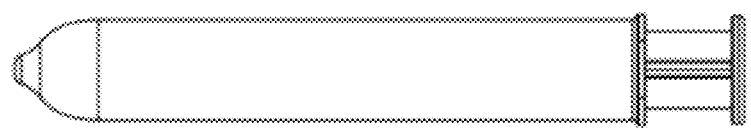 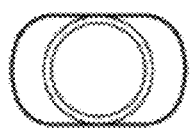
FIG. 6D     FIG. 6A     FIG. 6E
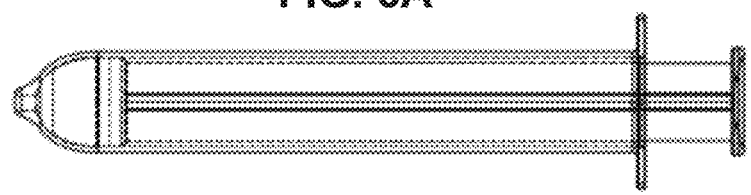
FIG. 6C
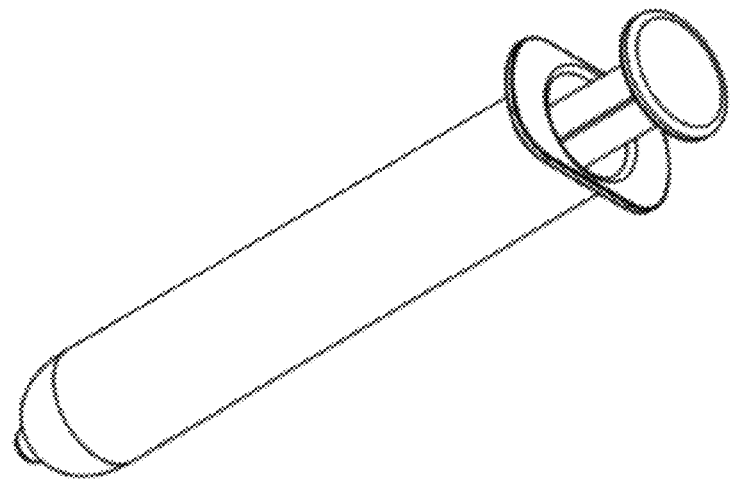
FIG. 6F

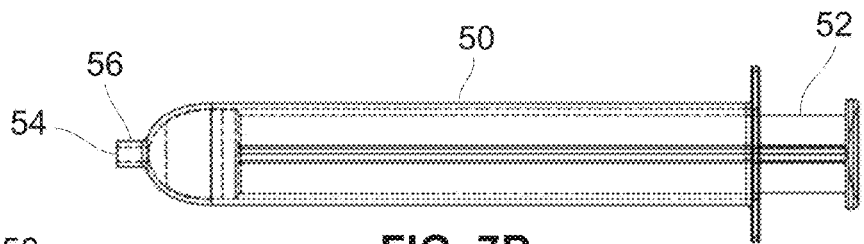
FIG. 7B
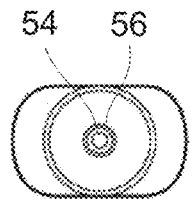
FIG. 7D
FIG. 7A
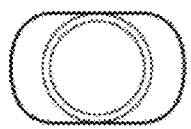
FIG. 7E
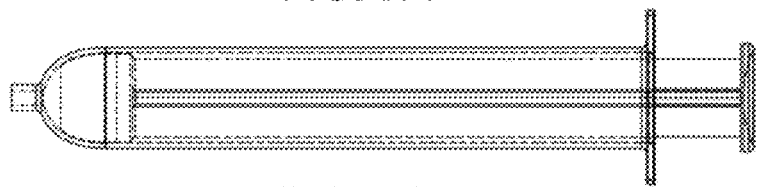
FIG. 7C
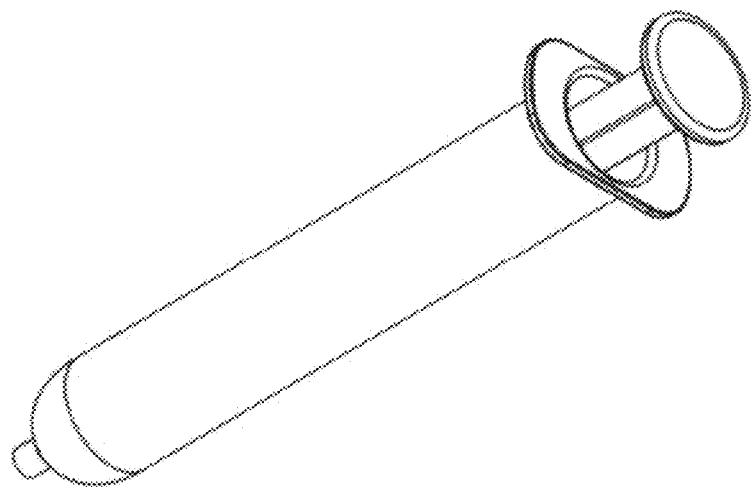
FIG. 7F

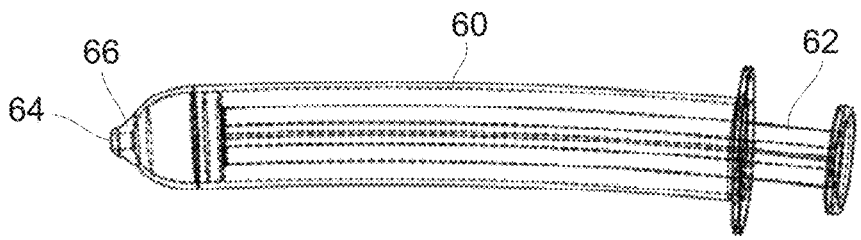
FIG. 8B
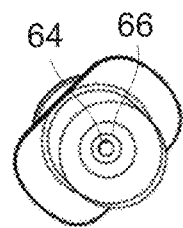
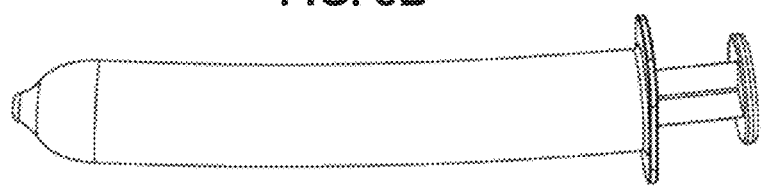
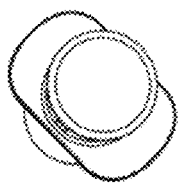
FIG. 8D  FIG. 8A  FIG. 8E
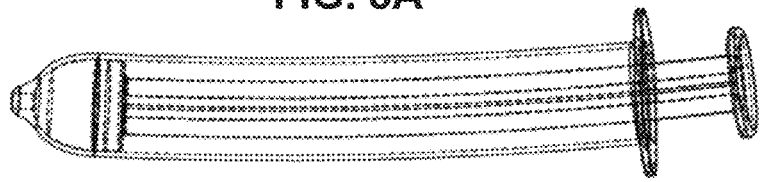
FIG. 8C
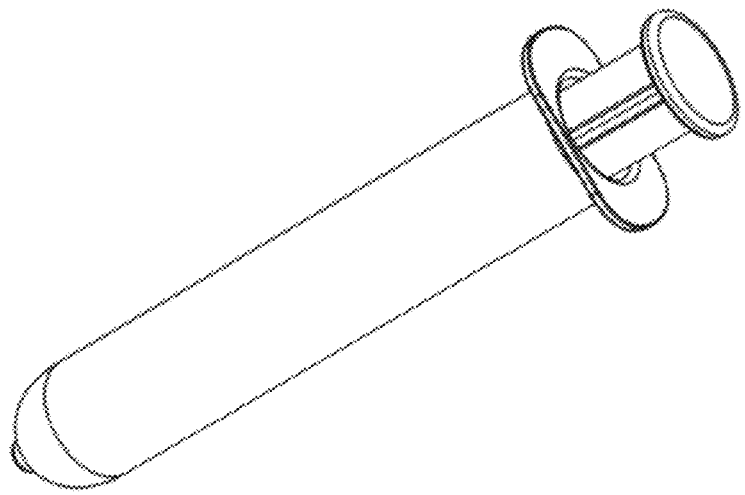
FIG. 8F

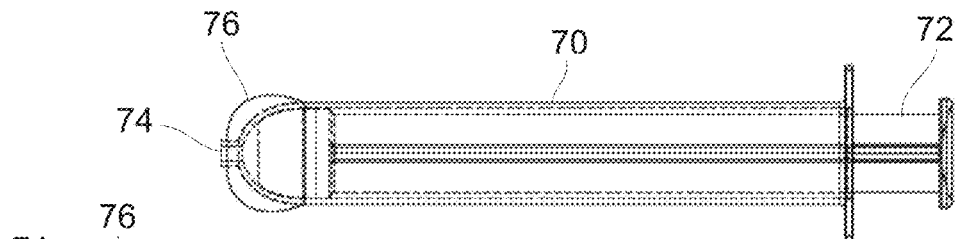
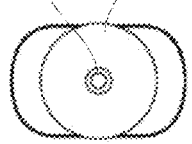
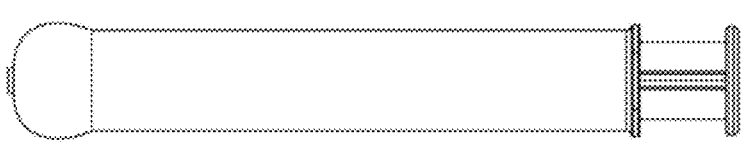
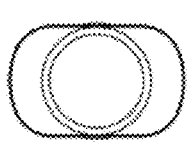
FIG. 9D     FIG. 9A     FIG. 9E
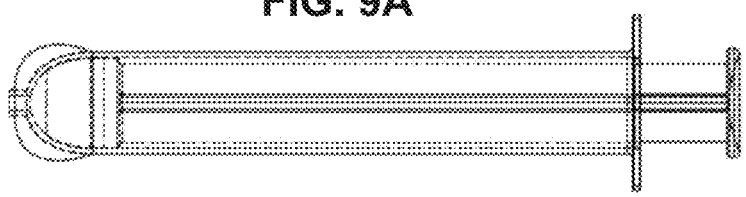
FIG. 9C
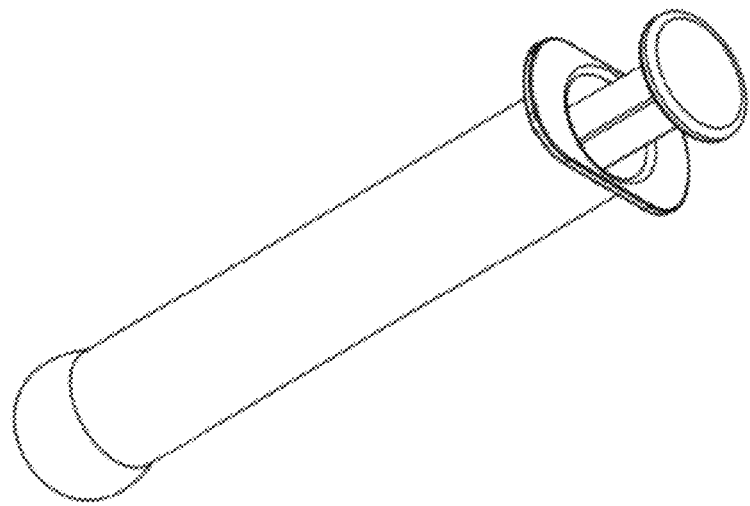
FIG. 9F

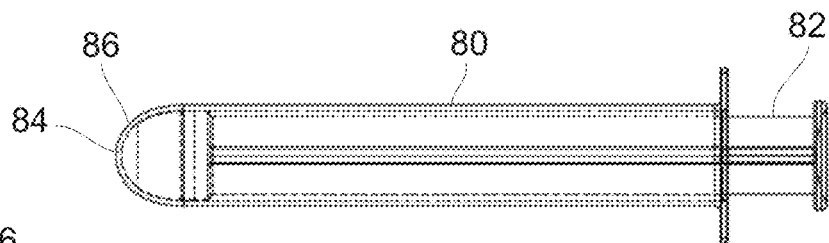
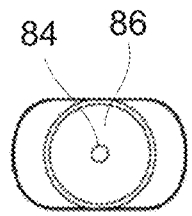
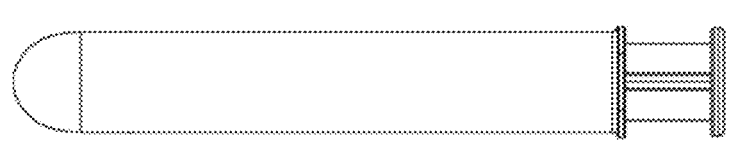
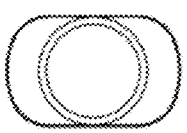
FIG. 10D    FIG. 10A    FIG. 10E
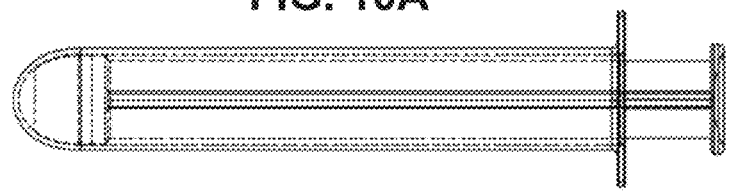
FIG. 10C
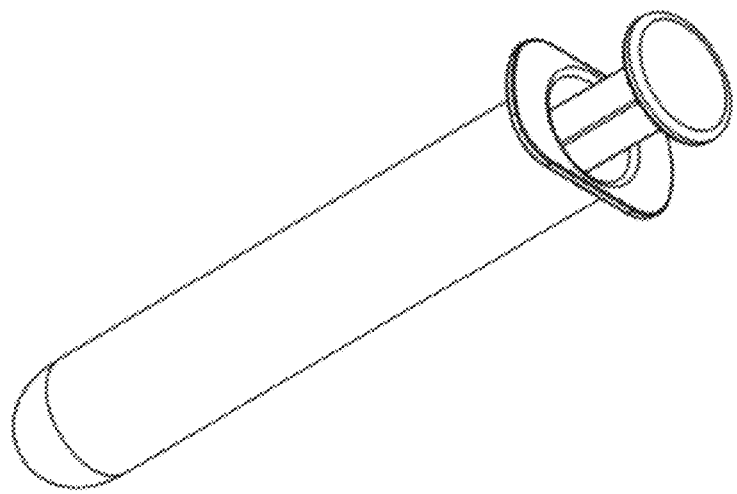
FIG. 10F

BODILY FLUID COLLECTION SYSTEM

CROSS-REFERENCE TO RELATED APPLICATIONS

This application claims the benefit of priority to U.S. Prov. Pat. App. 62/424,803 filed Nov. 21, 2016, which is incorporated herein by reference in its entirety.

FIELD OF THE INVENTION

The present invention relates to medical devices. In particular, the present invention relates to methods and apparatus for efficiently collecting bodily fluids such as semen within a syringe for use in an insemination procedure.

BACKGROUND OF THE INVENTION

For couples attempting to become pregnant, a number of fertility aids are commercially available. Generally, couples attempting pregnancy may utilize fertility aids after several cycles without success to improve their chances of becoming pregnant.

Once common method utilizes a commercially available syringe, such as a baster, for injecting semen directly within the vicinity of the cervix. In collecting the semen, the male may ejaculate into a clean or sterile glass or plastic cup, baggy, or collection condom. However, collecting this semen has several drawbacks when attempting to suction the ejaculate into the syringe. For instance, using a conventional glass or cup is inefficient because the flat surfaces of the glass or cup does not allow for the tips of conventional syringes to collect the entire volume of ejaculate when initially suctioning the ejaculate into the syringe for delivery. Attempting to do so will also damage the sperm contained within the ejaculate further possibly reducing the chances of pregnancy.

If the male ejaculates into a baggy or collection condom, attempting to suction the ejaculate into the syringe tip may also cause the baggy or condom to block the opening of the syringe tip, further reducing the volume of collected ejaculate and causing damage to the sperm contained within.

Aside from the use of commercially available syringes and cups, other fertility aids may be used such as a cervical cap or diaphragm. Such aids typically require the female to collect the semen within the cap or diaphragm and then insert the cap or diaphragm through the vagina and into contact against the cervix. However, such devices require that the female maintain the device in place for several hours.

Other options may also include a cervical cap with tube. These devices are used in the same manner as a cervical cap or diaphragm but add the further complication of injecting the sperm through a tube after a catheter is in place.

Accordingly, there remains a need for a sperm collection system which efficiently optimizes the collection of sperm and transfer into a syringe with minimal damage to the sperm.

SUMMARY OF THE INVENTION

A system for collecting and transferring sperm into a syringe may utilize a collection receptacle configured to receive a sample of bodily fluid such as ejaculate directly from a male and this ejaculate may be collected into a concentrated pool within the receptacle. The syringe is configured to have a distal collection tip which is gently tapered or radiused to present a smooth and atraumatic surface and which is specifically configured and shaped to be inserted within and received by the collection receptacle. The distal collection tip has a shape which corresponds directly to a tapered reservoir defined at the bottom of the collection receptacle such that a distal opening defined through the tip is optimally positioned within the concentrated bodily fluid pooled within the reservoir for collection. Moreover, the gentle taper of the collection tip may present an atraumatic surface for inhibiting damage to the sperm contained within the ejaculate as the sperm is suctioned into the distal opening for insemination into the female. The collection receptacle and syringe may be fabricated from any number of materials which are biocompatible, e.g., plastics, metals, etc., but are not so limited.

The collection receptacle may define an opening which is sufficiently large enough for a male to ejaculate directly into the receptacle, e.g., 2.5 in., and a collection portion which extends from a rim which defines the opening. The opening may be circular or it may be optionally formed into other various configurations. The collection portion may form a cup which is tapered from a first diameter defined by the rim and reduces to an apex forming a tapered reservoir, e.g., conically-shaped, such that the collection portion has a depth of, e.g., 1.7 in. or more. While the collection portion is shown to have a conical shape, the portion is not so limited but may form other shapes so long as the reservoir is formed to have a reduced diameter. This is so that the ejaculate or other bodily fluid which is introduced into the collection portion may slide down the walls of the portion and collect into a single concentrated pool within the reservoir thereby ensuring that the ejaculate and sperm is collected within a single pool.

The syringe may have a plunger assembly slidingly positioned within a syringe lumen such that proximal retraction of the plunger assembly relative to the syringe body may form a suction force through the distal opening for drawing the sperm into the lumen for insemination into the female and distal translation of the plunger assembly relative to the syringe body may urge the collected sperm distally out through the distal opening for introduction into the female. Because the syringe when held is used to collect the sperm from the collection receptacle and is also used to inject the sperm into the vagina of the female, the syringe may be sized accordingly to prevent trauma to the female but still large enough to facilitate manipulation of the syringe. Hence, the syringe may have a diameter of, e.g., 0.5 to 1.0 in. or larger, and a length of, e.g., 5.5 to 7.0 in. or larger.

The distal portion of the syringe may define a gentle taper which narrows to the collection tip which may have a diameter of, e.g., 0.1 to 0.5 in., and which defines the distal opening which may have a diameter of, e.g., 0.03 to 0.06 in. or larger. The distal portion may present a gentle radiused surface which is optionally radiused inward towards the syringe and which then inverts to a gentle radiused surface which is radiused outward along the collection tip to terminate at the distal opening. Alternatively, the distal portion may present a gentle radiused surface which presents a semispherical or curved surface which corresponds to the shape of the collection receptacle.

Because of the curvature of the distal portion and the collection tip, the distal opening may be positioned directly into a pool of the ejaculate which collects in a single location of the collection portion within the reservoir. Thus, the reservoir is configured and sized to receive the collection tip in a corresponding manner so that the distal opening is positionable directly against the bottom of the reservoir. This ensures that the sperm introduced through the opening of the collection receptacle flows down into the reservoir in a single concentrated pool such that the user may then introduce the collection tip and distal opening directly into the concentrated pool and suction the entirety of the collected sperm into the distal opening by drawing a suction via the plunger. This also ensures that all (or most) of the collected sperm is captured in a single draw of the plunger and also helps to preserve the integrity of the sperm by preventing damage. Once the sperm has been suitably drawn into the syringe, the syringe may then be introduced into the vagina and into proximity of the cervix for insemination.

In one embodiment, the fluid collection system may generally comprise a syringe having a body and a tapered collection tip which projects distally from the body and terminates in a distal opening; and a collection receptacle defining an opening which is sized for receiving a bodily fluid directly from a subject; a collection portion formed within the receptacle and forming a tapered body which terminates in a reservoir such that the bodily fluid deposited within the collection portion pools within the reservoir, wherein a shape of the reservoir corresponds with a shape of the collection tip of the syringe such that the bodily fluid within the reservoir is able to be drawn into the distal opening of the syringe.

In another embodiment, a fluid collection kit may generally comprise a syringe having a body, a distal portion, and a tapered collection tip which projects distally from the body and terminates in a distal opening, wherein the distal portion defines a radiused surface which is radiused inward towards the body and further defines an inverted radiused surface which is radiused outward along the collection tip; and a collection receptacle defining an opening which is sized for receiving a bodily fluid directly from a subject; a collection portion formed within the receptacle and forming a tapered conical body which tapers from a first diameter and terminates in a reservoir such that the bodily fluid deposited within the collection portion pools within the reservoir, wherein a shape of the reservoir corresponds with a shape of the collection tip of the syringe such that the bodily fluid within the reservoir is able to be drawn into the distal opening of the syringe.

In one method of collecting the bodily fluid, the method may generally comprise positioning a collection receptacle containing a bodily fluid such that the bodily fluid pools within a reservoir defined by a collection portion within the receptacle, wherein the collection portion forms a tapered body which terminates in the reservoir; positioning a distal opening of a syringe into the bodily fluid within the reservoir, the syringe having a body and a tapered collection tip which projects distally from the body and terminates in the distal opening, wherein a shape of the reservoir corresponds with a shape of the collection tip of the syringe; and drawing the bodily fluid into the syringe through the distal opening.

BRIEF DESCRIPTION OF THE DRAWINGS

FIGS. 5A and 5B show side and top views of a collection receptacle define one or more grooves or channels within the collection portion.

FIG. 5C shows a side view of another variation of the collection receptacle having an angled rim an optional lid.

FIGS. 6A to 6F show side, front, back, and perspective views of one variation of the syringe.

FIGS. 7A to 7F show side, front, back, and perspective views of another variation of the syringe.

FIGS. 8A to 8F show side, front, back, and perspective views of another variation of the syringe.

FIGS. 9A to 9F show side, front, back, and perspective views of another variation of the syringe.

FIGS. 10A to 10F show side, front, back, and perspective views of another variation of the syringe.

DETAILED DESCRIPTION OF THE INVENTION

Figure 1A:
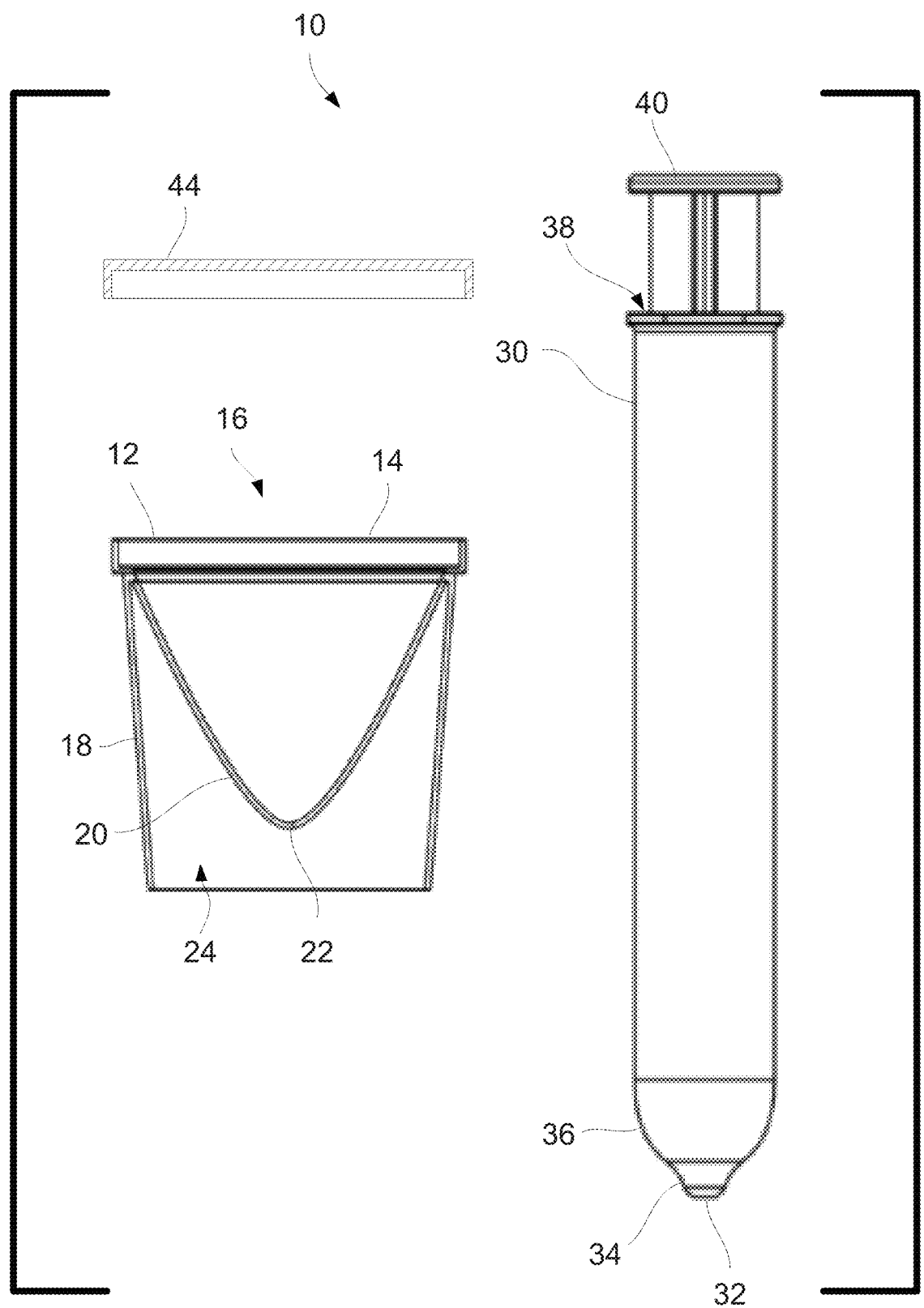
FIG. 1A shows a bodily fluid collection system having at least a collection receptacle and a syringe with collection tip which are configured to inter-fit with one another.

A system for collecting and transferring sperm into a syringe is shown in the side view of assembly 10 of FIG. 1A. The collection receptacle 12 is configured to receive a sample of bodily fluid such as ejaculate directly from a male and to collect the ejaculate into a concentrated pool within the receptacle 12, e.g., when the receptacle 12 is held in an upright position. The syringe 30 is configured to have a distal collection tip 34 which is gently tapered or radiused to present a smooth and atraumatic surface and which is specifically configured and shaped to be inserted within and received by the collection receptacle 12. The distal collection tip 34 has a shape which corresponds directly to a tapered reservoir 22 defined at the bottom of the collection receptacle 12 such that a distal opening 32 defined through the tip 34 is optimally positioned within the concentrated bodily fluid pooled within the reservoir 22 for collection. Moreover, the gentle taper of the collection tip 34 may present an atraumatic surface for inhibiting damage to the sperm contained within the ejaculate as the sperm is suctioned into the distal opening 32 for insemination into the female. The collection receptacle 12 and syringe 30 may be fabricated from any number of materials which are biocompatible, e.g., plastics, metals, etc., but are not so limited.

The collection receptacle 12 may define an opening 16 which is sufficiently large enough for a male to ejaculate directly into the receptacle 12, e.g., 2.5 in., and a collection portion 20 which extends from a rim 14 which defines the opening 16. The opening 16 may be circular or it may be optionally formed into other various configurations. In either case, the receptacle 12 may also include a cap or cover 44 which is sized for securement over or upon the rim 14 so that any collected ejaculate or other specimen may be covered for facilitating handling and/or transportation of the receptacle 12, e.g., a user may collect ejaculate within the receptacle 12 and secure it with cap or cover 44 for delivery to a practitioner or laboratory. Additionally, the cap or cover 44 may be separate from the receptacle 12 or it may be attached using any number of mechanisms, e.g., pivoted, hinged, wire, string, etc. The collection portion 20 may form a cup which is tapered from a first diameter defined by the rim 14 and reduces to an apex forming a tapered reservoir 22, e.g., conically-shaped, such that the collection portion 20 has a depth of, e.g., 1.7 in. or more. While the collection portion 20 is shown to have a conical shape, the portion 20 is not so limited but may form other shapes so long as the reservoir 22 is formed to have a reduced diameter. This is so that the ejaculate or other bodily fluid which is introduced into the collection portion 20 may slide down the walls of the portion 20 and collect into a single concentrated pool within the reservoir 22 thereby ensuring that the ejaculate and sperm is collected within a single pool.

A supporting wall 18 may extend around the receptacle 12 and have a length, e.g., 2.5 in., to provide a support for positioning the receptacle 12 upon a flat surface after collection of the sperm. Moreover, the wall 18 may form a hollowed out region 24 between the wall 18 and collection portion 20, e.g., to save on weight. Furthermore, the bottom of the reservoir 22 of the collection portion 20 may be sized to maintain a separation or distance from the edge of the bottom rim so that the collection portion 20 is removed or separated at a distance from any table or surface that the receptacle 12 may be placed upon.

Additionally, because the hollowed out region 24 between the wall 18 and collection portion 20 provides for a limited contact region along the rim 14, the collection portion 20 may be relatively thermally isolated from the wall 18 (particularly during handling) and from any surface that receptacle 12 may be placed upon. This enables the collection portion 20 to maintain a more thermally stable environment and in turn reduces thermal fluctuations (particularly during handling of the receptacle 12) in any of the collected material contained within the collection portion 20. Maintaining a stable thermal environment may improve the collection and survival rates of sperm post ejaculation especially, e.g., if a user is collecting samples at one location (such as their home) to bring samples into a clinic or laboratory for processing.

Turning now to the syringe 30, a plunger assembly 40 may be slidingly positioned within a syringe lumen 38 such that proximal retraction of the plunger assembly 40 relative to the syringe body 30 may form a suction force through the distal opening 32 for drawing the sperm into the lumen 30 for insemination into the female and distal translation of the plunger assembly 40 relative to the syringe body 30 may urge the collected sperm distally out through the distal opening 32 for introduction into the female. Because the syringe 30 when held is used to collect the sperm from the collection receptacle 12 and is also used to inject the sperm into the vagina of the female, the syringe 30 may be sized accordingly to prevent trauma to the female but still large enough to facilitate manipulation of the syringe 30. Hence, the syringe 30 may have a diameter of, e.g., 0.5 to 1.0 in. or larger, and a length of, e.g., 5.5 to 7.0 in. or larger.

The distal portion 36 of the syringe 30 may define a gentle taper which narrows to the collection tip 34 which may have a diameter of, e.g., 0.1 to 0.5 in., and which defines the distal opening 32 which may have a diameter of, e.g., 0.03 to 0.06 in. or larger. In the variation shown, the distal portion 36 may present a gentle radiused surface which is radiused inward towards the syringe 30 and which then inverts to a gentle radiused surface which is radiused outward along the collection tip 34 to terminate at the distal opening 32.

Figure 1B:
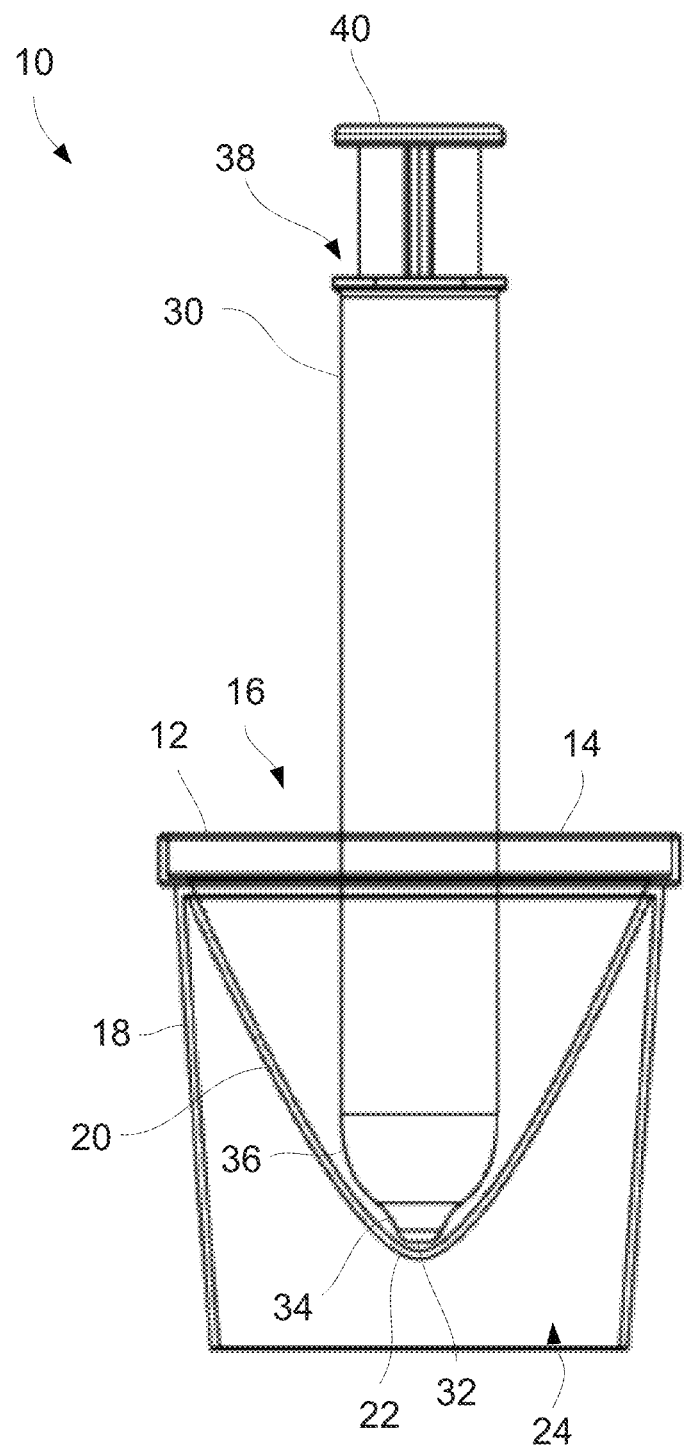
FIG. 1B shows a side view of the collection tip of the syringe positioned within the collection reservoir of the receptacle.

Turning now to FIG. 1B, the collection tip 34 is shown inserted and positioned within the reservoir 22 of collection portion 20. Because of the curvature of the distal portion 36 and the collection tip 34, the distal opening 32 may be positioned directly into a pool of the ejaculate which collects in a single location of the collection portion 20 within the reservoir 22. Thus, the reservoir 22 is configured and sized to receive the collection tip 34 in a corresponding manner so that the distal opening 32 is positionable directly against the bottom of the reservoir 22. This ensures that the sperm introduced through the opening 16 of the collection receptacle 12 flows down into the reservoir 22 in a single concentrated pool such that the user may then introduce the collection tip 34 and distal opening 32 directly into the concentrated pool and suction the entirety of the collected sperm into the distal opening 32 by drawing a suction via the plunger 40. This also ensures that all (or most) of the collected sperm is captured in a single draw of the plunger 40 and also helps to preserve the integrity of the sperm by preventing damage. Once the sperm has been suitably drawn into the syringe 30, the syringe 30 may then be introduced into the vagina and into proximity of the cervix for insemination.

Figure 2A:
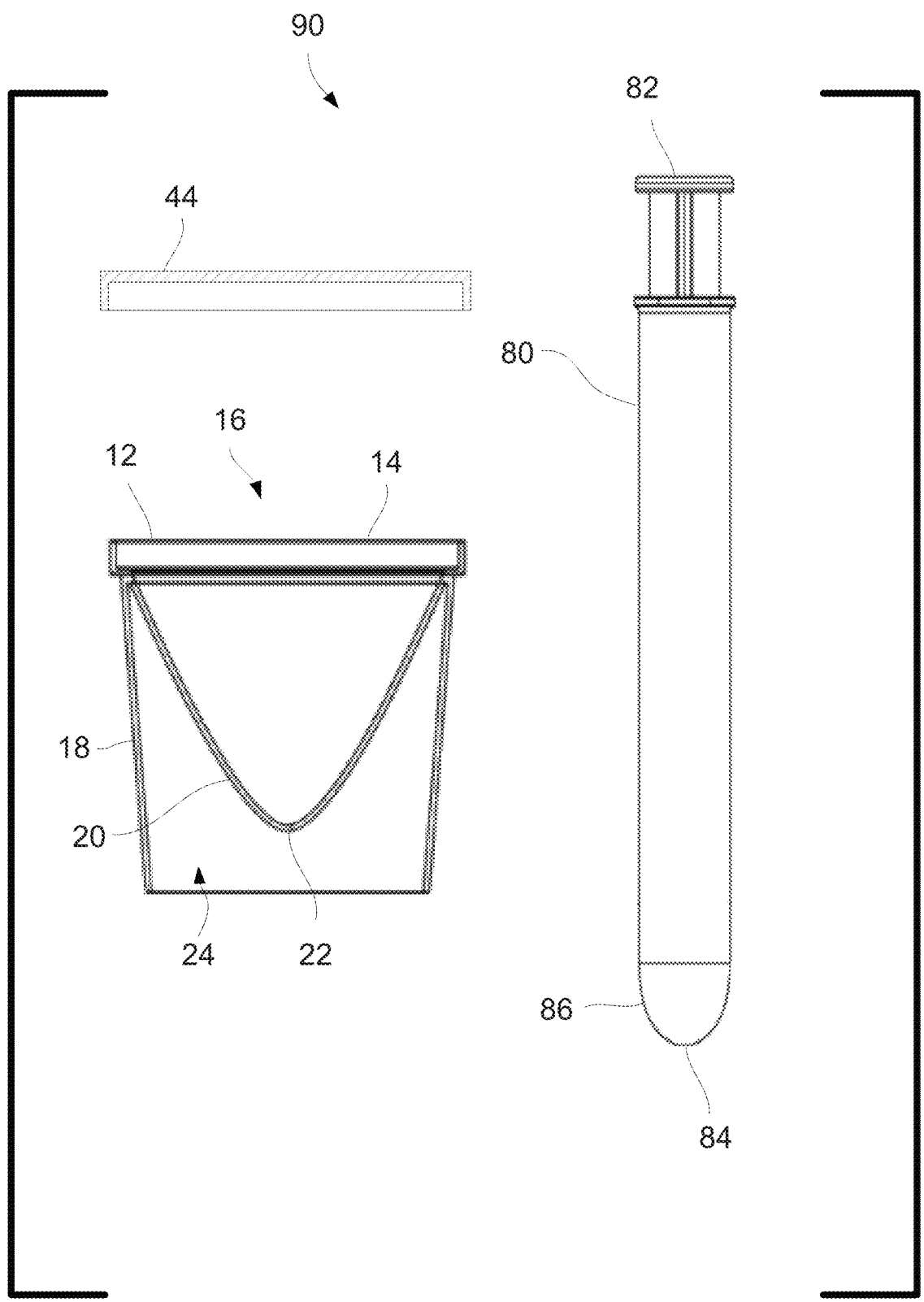
FIG. 2A shows another variation of the bodily fluid collection system having at least a collection receptacle and a syringe with collection tip which are configured to inter-fit with one another.
Figure 2B:
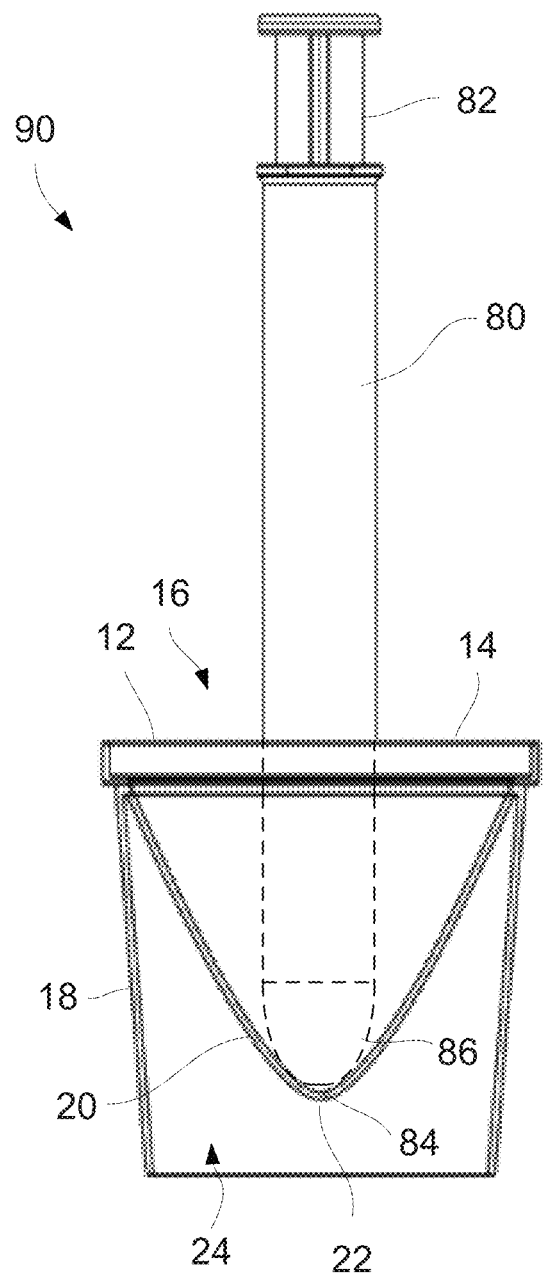
FIG. 2B shows a side view of the collection tip of the syringe of FIG. 2A positioned within the collection reservoir of the receptacle.

FIG. 2A shows a side view of another variation of the system 90 for collecting and transferring sperm into the syringe. In this variation, the syringe 80 may omit the distal collection tip 34 and instead present a distal portion 86 which is semispherical or curved in shape leading to the opening 84. Even with the distal portion 86 omitting the collection tip 34, the opening 84 may still be fully inserted into the concentrated pool within the reservoir 22 of the collection portion 20 so long as the shape of the distal portion 86 and the reservoir 22 are correspondingly shaped and/or curved relative to one another to optimize the collection of ejaculate into the syringe 80 through opening 84.

Figure 3A:
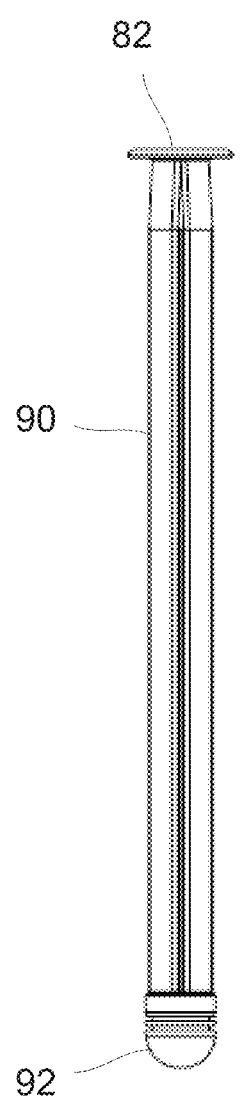
FIGS. 3A and 3B show side and perspective views of a plunger having a hemispherical or curved surface defined over the plunger tip.
Figure 3B:
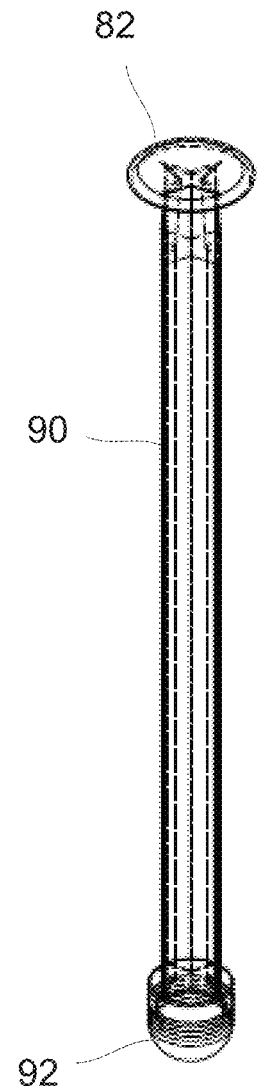

One variation of a plunger 82 which is configured for use with the syringe 80 may be seen in the side and perspective views of FIGS. 3A and 3B. In this variation, the plunger 82 may have an elongate shaft 90 which is used to urge a plunger tip 92 which is shaped to conform to the inner surface of the distal portion 86 of the syringe barrel. Here, the plunger tip 92 may be shaped to form a hemispherical or curved surface which seals against the inner surface of the barrel when urged distally or proximally but particularly when urged fully distal into contact against the interior of the distal portion 86. In this manner, the plunger tip 92 may fully draw the ejaculate or other bodily fluid into the syringe barrel and fully discharge the ejaculate or fluid from the curved interior of the distal portion 86 to optimize the volume of fluid discharge while presenting a gentle surface to minimize any damage to the cells within the ejaculate.

Figure 4B:
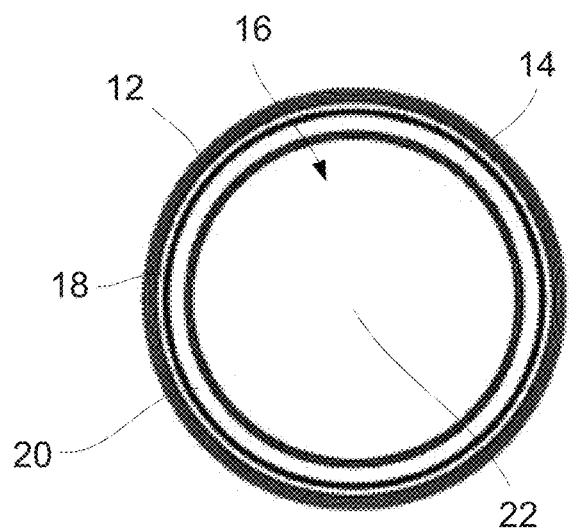
FIGS. 4A to 4C show side, top, and perspective views of the collection receptacle.
Figure 4C:
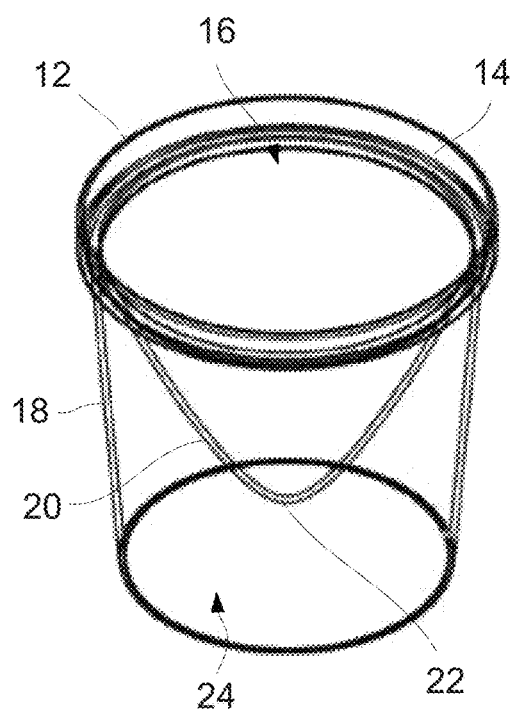
Figure 4A:
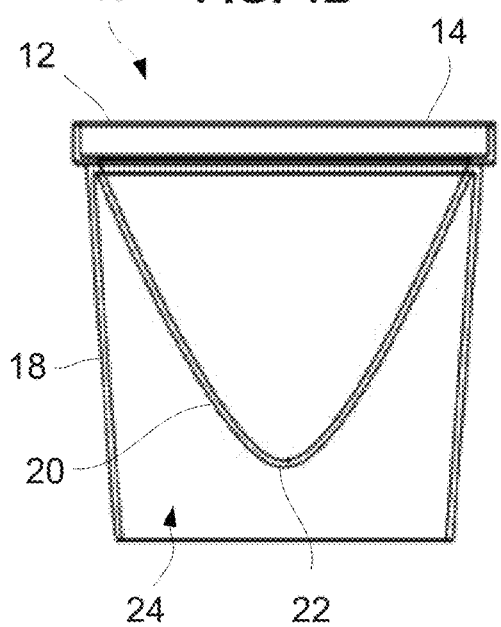

FIGS. 4A to 4C show side, top, and perspective views of the collection receptacle 12. As shown, the walls 18 may present a support for the collection portion 20 which may form, e.g., an inverted conical shape which terminates in the reservoir 22 located at the apex of the portion 20. After the male has ejaculated within the receptacle 12, the user may position the receptacle 12 upon a flat surface such as a table so that the sperm may flow down the sides of the portion 20 and collect in a concentrated pool within the single reservoir 22. As discussed above, the user may then introduce the collection tip 34 of the syringe 30 into the reservoir 22 for drawing up the sperm.

Another variation of the collection receptacle is shown in the side and top views of FIGS. 5A and 5B which illustrates a receptacle having the collection portion 20 and walls 18, as previously described. Yet in this variation, the collection portion 20 may define one or more grooves or channels 21 which may extend radially from the reservoir 22. These grooves or channels 21 may be formed at least partially along the length of the collection portion 20 and they may be uniformly or asymmetrically spaced apart from one another so long as they extend from an upper region of the collection portion 20 to the reservoir 22. Moreover, while the top view of FIG. 5B shows four radially spaced grooves or channels 21, a single channel 21 may be defined or more than four channels 21 may be defined, as practicable.

Because the distal portion of the syringe 86 is designed to correlate to the reservoir 22 and collection portion 20, the grooves or channels 21 may allow for ejaculate or other bodily fluid to flow through the channels 21 and into the reservoir 22 particularly when the syringe 80 is positioned within the receptacle 12 for collection. With the close fit, the ejaculate or bodily fluid may still flow past the contact region between the syringe 80 and collection portion 20 via the channels 21 and into the reservoir 22 for suctioning into the opening 84 of the syringe 80. In this manner, the volume of fluid drawn into the syringe 80 is optimized. Moreover, the use of the grooves or channels 21 may be incorporated into any of the collection receptacle embodiments described herein.

FIG. 5C shows yet another variation where the collection receptacle may define a rim 23 which is tapered or angled relative to the collection portion 20 which may facilitate the insertion and/or removal of the syringe 80 from the receptacle. Additionally and/or optionally, the receptacle may incorporate a lid or cover 25 which may be temporarily secured upon the rim 23. This lid or cover 25 may be optionally attached to the collection receptacle via a coupling mechanism such as a pivot or hinge, e.g., living hinge, mechanical hinge, etc. The use of the angled rim 23 and/or lid or cover 25 may be incorporated into any of the collection receptacles described herein.

FIGS. 6A to 6C show various side views of one variation of the syringe 30 while FIGS. 6D and 6E show front and rear views of the syringe 30. FIG. 6F shows a perspective view of the syringe 30. As discussed above, this variation of the syringe 30 may have the gently tapered collection tip 34 terminate in the distal opening 32. A plunger tip 42 may be seen in the side views of FIGS. 6B and 6C positioned at the distal end of the plunger 40 for sliding through the syringe barrel.

FIGS. 7A to 7C show various side views of another variation of the syringe 50 while FIGS. 7D and 7E show front and rear views of the syringe 50. FIG. 7F shows a perspective view of the syringe 50. In this variation, syringe 50 may have a plunger 52 and a collection tip 56 which is terminates in a distal opening 54. The collection tip 56 may be formed in a tubular configuration which projects from the syringe body. The tubular configuration of the collection tip 56 allows for the insertion of the distal opening 54 into the reservoir 22 of the receptacle 12.

FIGS. 8A to 8C show various side views of another variation of the syringe 60 while FIGS. 8D and 8E show front and rear views of the syringe 60. FIG. 8F shows a perspective view of the syringe 60. In this variation, syringe 60 may have a plunger 62 and a collection tip 66 which is terminates in a distal opening 64 which is configured similarly to the variation shown in FIGS. 6A to 6E above. However, this variation may have a syringe body which presents a gentle curved or arcuate shape to facilitate insertion of the syringe 60 into the vagina for insemination once the sperm has been suctioned into the syringe 60.

FIGS. 9A to 9C show various side views of another variation of the syringe 70 while FIGS. 9D and 9E show front and rear views of the syringe 70. FIG. 9F shows a perspective view of the syringe 70. In this variation, syringe 70 may have a plunger 72 and a collection tip 74 which is terminates in a distal opening. However, this variation may also incorporate an enlarged interface 76 which may form a bulbous or enlarged curved surface which projects from a distal end of the syringe 70. The collection tip 74 may project through and from the interface 76 and the interface 76 may present a hard surface or a softened surface which flexes when contacted against the patient. Furthermore, with this variation of the syringe 70, the collection receptacle may be enlarged to receive the enlarged interface 76 although the collection portion may still be tapered to ensure that the collected sperm pools within the reservoir.

FIGS. 10A to 10C show various side views of another variation of the syringe 80 while FIGS. 10D and 10E show front and rear views of the syringe 80. FIG. 10F shows a perspective view of the syringe 80. In this variation, syringe 80 may have a plunger 82 and a distal portion 86 which is terminates in a distal opening 84 without a collection tip. Because the collection tip is omitted in this configuration, the collection receptacle may be slightly enlarged to receive the distal portion 86 of the syringe 80 although the collection portion may still be tapered to ensure that the collected sperm pools within the reservoir.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A fluid collection system, comprising:
  a syringe having a body and a distal portion having a first curvature which defines a distal opening; and
  a collection receptacle defining an opening which is sized for receiving a bodily fluid directly from a subject;
  a collection portion formed within the receptacle and forming a tapered body which terminates in a reservoir having a second curvature such that the bodily fluid deposited within the collection portion pools within the reservoir, wherein a shape of the second curvature of the reservoir corresponds directly with a shape of the first curvature of the distal portion of the syringe such that the distal opening is directly positioned within the bodily fluid within the reservoir when the distal portion of the syringe is inserted into the collection receptacle due to the first curvature and the second curvature corresponding to one another so that the bodily fluid is able to be drawn into the distal opening of the syringe.

2. The system of claim 1 wherein the body of the syringe defines a curved or arcuate shape.

3. The system of claim 1 wherein the distal portion of the syringe further comprises a tapered collection tip which projects and terminates in the distal opening.

4. The system of claim 3 wherein collection tip defines a radiused surface which is radiused inward towards the body and further defines an inverted radiused surface which is radiused outward along the collection tip.

5. The system of claim 1 wherein the collection portion forms a conical shape which tapers from a first diameter defined by a rim and reduces to an apex forming the reservoir.

6. The system of claim 1 wherein the collection receptacle further comprises a support wall which surrounds the collection portion.

7. The system of claim 1 wherein the collection portion defines one or more grooves or channels at least partially along the collection portion and extending to the reservoir.

8. The system of claim 1 wherein the collection receptacle defines a rim which is angled or tapered relative to the collection portion.

9. The system of claim 1 further comprises a lid which is coupled to the collection receptacle.

10. A fluid collection kit, comprising:
a syringe having a body and a distal portion which defines a distal opening, wherein the distal portion defines a radiused surface having a first shape; and
a collection receptacle defining an opening which is sized for receiving a bodily fluid directly from a subject;
a collection portion formed within the receptacle and forming a tapered conical body which tapers from a first diameter and terminates in a reservoir having a second shape such that the bodily fluid deposited within the collection portion pools within the reservoir, wherein the second shape of the reservoir corresponds directly with the first shape of the collection tip of the syringe such that the distal opening is directly positioned within the bodily fluid within the reservoir when the distal portion of the syringe is inserted into the collection receptacle due to the first curvature and the second curvature corresponding to one another so that the bodily fluid is able to be drawn into the distal opening of the syringe.

11. The kit of claim 10 wherein the distal portion further comprises a tapered collection tip which is radiused inward towards the body and further defines an inverted radiused surface which is radiused outward along the collection tip.

12. A method of collecting a bodily fluid, comprising:
positioning a collection receptacle containing a bodily fluid such that the bodily fluid pools within a reservoir defined by a collection portion having a receiving shape within the receptacle, wherein the collection portion forms a tapered body which terminates in the reservoir;
positioning a distal opening of a syringe into the bodily fluid within the reservoir, the syringe having a body and a distal portion having a collection shape which defines the distal opening, wherein the receiving shape of the reservoir corresponds directly with the collection shape of the syringe such that the distal opening is directly positioned within the bodily fluid when the distal portion of the syringe is inserted into the collection receptacle due to the receiving shape of the reservoir and the collection shape of the syringe corresponding to one another; and
drawing the bodily fluid into the syringe through the distal opening.

13. The method of claim 12 wherein the distal portion of the syringe further comprises a tapered collection tip which projects and terminates in the distal opening.

14. The method of claim 13 wherein a distal portion of the syringe defines a radiused surface which is radiused inward towards the body and further defines an inverted radiused surface which is radiused outward along the collection tip.

15. The method of claim 12 wherein the collection portion forms a conical shape which tapers from a first diameter defined by a rim and reduces to an apex forming the reservoir.

16. The method of claim 12 further comprising receiving the bodily fluid within the collection receptacle directly from a subject prior to positioning a collection receptacle.

17. The method of claim 16 wherein receiving the bodily fluid comprises receiving an ejaculate from the subject directly within the collection receptacle.

18. The method of claim 12 wherein drawing the bodily fluid comprises capturing at least a majority of the bodily fluid into the syringe.

19. The method of claim 12 wherein the collection portion defines one or more grooves or channels at least partially along the collection portion and extending to the reservoir.

20. The method of claim 12 wherein the collection receptacle defines a rim which is angled or tapered relative to the collection portion.

* * * * *